United States Patent [19]

Wang

[11] Patent Number: 4,473,650

[45] Date of Patent: Sep. 25, 1984

[54] USE OF STRONG ORGANIC ACID POLYELECTROLYTE SALTS IN TEST MEANS, TEST DEVICE AND METHOD FOR DETERMINING THE IONIC STRENGTH OR SPECIFIC GRAVITY OF A LIQUID SAMPLE

[75] Inventor: Joseph Y. Wang, Elkhart, Ind.

[73] Assignee: Miles Laboratories, Inc., Elkhart, Ind.

[21] Appl. No.: 453,766

[22] Filed: Dec. 27, 1982

[51] Int. Cl.$^3$ .................. G01N 9/36; G01N 33/52
[52] U.S. Cl. .................................. 436/2; 73/32 R; 422/56; 427/2; 436/163; 436/169
[58] Field of Search ............ 422/56, 57; 436/2, 163, 436/164, 169; 73/32 R; 427/2

[56] References Cited

U.S. PATENT DOCUMENTS 3,449,080  6/1969  Edwards ........................ 422/56 X
4,318,709  3/1982  Falb et al. ...................... 422/56 X
4,376,827  3/1983  Stiso et al. .......................... 436/2

FOREIGN PATENT DOCUMENTS 2037981  7/1980  United Kingdom ............ 73/32 R

Primary Examiner—Arnold Turk
Assistant Examiner—Robert J. Hill, Jr.
Attorney, Agent, or Firm—Edward H. Gorman, Jr.

[57] ABSTRACT

An improved test means, device and method for determining the ionic strength or specific gravity of an aqueous sample are disclosed. The test means comprises a weakly basic polyelectrolyte polymer salt and an indicator means capable of producing a detectable response to ion exchange between the polymer salt and the test sample. The polymer salt is one in which one or more of the basic moieties of the polymer is present as the salt of a strong organic acid.

12 Claims, No Drawings

USE OF STRONG ORGANIC ACID POLYELECTROLYTE SALTS IN TEST MEANS, TEST DEVICE AND METHOD FOR DETERMINING THE IONIC STRENGTH OR SPECIFIC GRAVITY OF A LIQUID SAMPLE

CONTENTS

1. Introduction
    1.1 Applications of the Invention
    1.2 Relationships betweens specific Gravity and Ionic Strength
2. Background of the Invention
3. Summary of the Invention
4. Definitions
5. Polyelectrolytes and Their Salts
    5.1 Weakly Basic Polyelectrolytes
    5.2 Strong Organic Acids
    5.3 Preparation of the Polyelectrolyte Salt
6. pH Indicator Means
7. The Test Device
    7.1 The Carrier Matrix
    7.2 Incorporation of the Matrix with the Composition
    7.3 Preparation of a Dip-and-Read Device
8. Reference Standard
9. Examples
    9.1 Preparation of the Polyelectrolyte Salt
    9.2 Preparation of Test Devices
    9.3 Evaluation of the Test Device

INTRODUCTION

The present invention relates to the determination of the ionic strength or specific gravity of a test sample. A test means, test device and method are disclosed for making this determination in an aqueous test sample. These aspects of the invention provide a simple, facile method for analyzing ionic strength or specific gravity whereby results are available to the assayist momentarily after merely contacting a test sample solution with the test means or device. There is no need for such cumbersome apparatuses and procedures as hydrometers, urinometers, gravimeters, calibration, the cleaning of equipment, or other trappings of prior procedures.

Application of the Invention

The determination of the specific gravity of a liquid has application in numerous arts. Such seemingly unrelated disciplines as brewing, urinalysis, water purification, and the preparation of drinking water aboard a ship at sea all involve the measurement of specific gravity. Needless to say, a quick, facile method for determining this solution property would greatly enhance the state of these technologies, as well as any others where rapid, accurate determination of specific gravity would be beneficial. Thus, for example, if a medical laboratory technician could accurately measure the specific gravity of a urine sample in a matter of seconds, not only would such rapid results aid the physician in diagnosis, but also laboratory efficiency would increase manyfold.

Although the present invention lends itself to a vast range of applications, for purposes of clarity this discussion will be couched largely in terms of the determination of the ionic strength or specific gravity of urine. Applications to other disciplines will become apparent from an understanding of how this invention relates to urinalysis.

The determination of urine specific gravity is of considerable value in the understanding and clinical management of electrolyte disturbances. Hence, complete urinalysis should, and usually does, include a specific gravity determination. Generally, such a determination would include the measurement of specific gravity directly with a suitable device, but equally useful is the measurement of some related property, such as osmolality or ionic strength, which can then be referred back to corresponding specific gravity values.

Relationship Between Specific Gravity and Ionic Strength

Specific gravity is a dimensionless term and relates, in the case of a solution, to the ratio of the weight of a certain volume of the solution at a given temperature to that of an equal volume of water, also at some specified temperature. For solutions such as urine, the specific gravity is a function of the number, density, ionic charge, and weight of the various species of dissolved solutes.

The term "ionic strength" refers to the mathematical relationship between the number of different kinds of ionic species in a particular solution and their respective charges. Thus, ionic strength $\mu$ is represented mathematically by the formula $$\mu = \tfrac{1}{2} \sum_i c_i z_i^2 \tag{1}$$

in which c is the molal concentration of a particular ionic species and z the absolute value of its charge. The sum $\Sigma$ is taken over all the different kinds of ions in solution.

The relationship between ionic strength and specific gravity has a definable mathematical correlation. In the case of dilute NaCl, for example, in which the solution has a molal concentration of c, equation (1) reduces to $$\mu = \tfrac{1}{2} \sum_i c_i z_i^2 \tag{1}$$

$$= \tfrac{1}{2} [(c_{Na+})(1) + (c_{Cl-})(1)] \tag{2}$$

$$\mu = c \tag{3}$$

Moreover, it is known that the relationship between molality c and molarity M of a given solution is $$c = \frac{M}{\rho} \tag{4}$$

where $\rho$ is the density of the solvent. Substituting c from equation (3) into equation (4) yields the relationship between ionic strength and molarity.

$$\mu = \frac{M}{\rho} \tag{5}$$

For dilute NaCl, it has been found experimentally that the following relationships between molar concentration (M) and specific gravity (SG) exist:

| SG | ΔSG | M NaCl | ΔM |
|---|---|---|---|
| 1.005 |  | 0.120 |  |
|  | 0.005 |  | 0.120 |
| 1.010 |  | 0.240 |  |
|  | 0.005 |  | 0.120 |

| SG | ΔSG | M NaCl | ΔM |
|---|---|---|---|
| 1.015 | | 0.360 | |
| | 0.005 | | 0.128 |
| 1.020 | | 0.488 | |
| | 0.005 | | 0.125 |
| 1.025 | | 0.613 | |

The data shows that for every incremental increase of 0.12 M in NaCl concentration, a corresponding change in SG of 0.005 occurs. Using this relationship, SG can be defined mathematically as $$SG = 1 + \frac{0.005M}{0.12} \quad (6)$$

Substituting (5) into (6) we have $$SG = 1 + \frac{0.005\mu\rho}{0.12} \quad (7)$$

Where the solvent is water, $\rho=1$ and equation (7) reduces to $$SG = 1\frac{0.005\mu}{0.12} \quad (8)$$

BACKGROUND OF THE INVENTION

Prior to the present invention, most methods for determining specific gravity utilized hydrometers, urinometers, pycnometers, gravimeters and the like. Although these prior art procedures are satisfactorily sensitive in most cases, they involve fragile, bulky instruments which must be constantly cleaned, maintained, and calibrated in order to continuously assure their reliability. In addition, there are many inconveniences associated with the mechanics of using these instruments. There may be a difficulty in reading the miniscus. Froth or bubbles on the liquid surface may interfere with the reading. There is a tendency for urinometers to adhere to the sides of the vessel containing the liquid sample. In the case of urine, the sample quantity is frequently inadequate for accommodating one of the aforementioned devices.

A recent breakthrough in which all of the above disadvantages have been virtually eliminated, and which affords rapid osmolality (ergo, specific gravity) determination, is disclosed in U.S. Pat. No. 4,015,462, issued to Greyson, et al., and assigned to the present assignee. This patent describes an invention in which a carrier matrix is incorporated with osmotically fragile microcapsules, the walls of which are composed of a semi-permeable membrane material. Encapsulated inside the walls is a solution containing a coloring substance. When the capsules come in contact with a solution having a lower osmolality than that within the capsules, an osmotic gradient occurs across the capsule walls in the direction of the lower osmolality, thereby increasing the hydrostatic pressure within the capsules, thus causing them to swell and, ultimately, to rupture, releasing their colored contents. The amount of color formed from this phenomenon is a function of the specific gravity of the solution.

Thus, it is seen that, besides the numerous devices which measure specific gravity directly, it is also possible to measure specific gravity using an indirect means such as the osmolality of a solution.

Yet another way of estimating specific gravity without measuring it directly involves a determination which is proportional to the ionic strength of a solution, the correlation of which parameters has already been discussed in section 1.1, supra. Such an approach is utilized in U.S. Pat. No. 4,318,709 issued to Falb, et al., and assigned to the present assignee. Since it is well known that the specific gravity of an aqueous system is greatly affected by the presence of charged species, it is possible to closely approximate the specific gravity of the respective solutions via measurements proportional to their ionic strengths, and refer those measurements to a precalibrated reference system. The Falb, et al., patent makes use of such a relationship.

The Falb et al. patent discloses the use of weakly acidic or basic polyelectrolytes which have been at least 50% neutralized with a base (such as NaOH) or an acid (such as HCl), respectively. Depending on the ionic strength of the test solution, an intramolecular pH change may occur in the polymer, the degree of which is a barometer of ionic strength. A pH indicator such as a pH meter or pH-sensitive compound reflects the pH change (or lack thereof) instigated by the sample ionic strength.

Both the osmolality approach and the ionic strength approach to indirectly determining specific gravity could conceivably be affected insofar as accuracy is concerned by the presence of nonionic species. However, it has been found that such nonionic constituents as glucose, protein and urea do not effectively lead to anomalous or substantially inaccurate results with the Falb, et al. test except at very high concentrations. See Burkhardt, et al., Clinical Chemistry, 28, 2068–2072 (1982).

U.S. Pat. No. 4,108,727 is directed to a method for removing this potential source of inaccuracy, and discloses a device in which the specific gravity-sensitive system contains an ionizing agent capable of converting the nonionic solute to ionized species.

U.S. Pat. No. 3,449,080 discusses measuring dissolved sodium or chloride ions. This reference is directed to a test device for determining the concentrations of these ions in body sweat. There is disclosed in this patent the use of ion exchange resins together with a pH indicator. Using this device, the presence of sodium or chloride ions is said to be determined through a color change in the ion exchange resin caused by the pH indicator. Whereas this reference purports to disclose a way of measuring ionic strength, it was found by the present inventors that such teachings, as set forth in the examples, were inapplicable to the measurement of specific gravity.

To summarize the background of specific gravity measurement prior to the present invention, many methods are known for assaying that solution parameter, both direct and indirect. Direct measurement includes utilizing devices which are fragile, bulky and expensive, and which must be constantly cleaned, maintained and calibrated. Of the indirect methods, the measurement of the colligative solution property known as osmolality can provide an accurate correlation to specific gravity. In addition, the relationship between specific gravity and the ionic strength of a solution can be employed, by utilizing partially neutralized polyelectrolytes and a pH indicator. Weak polyelectrolytes are said to be useful in gauging the concentration of sodium and/or chloride ions in body sweat.

The present invention provides a departure from the prior art which enables dramatic improvements in the measurement of ionic strength, ergo specific gravity. Practice of the invention affords greater sensitivity in differentiating various specific gravity levels, as well as enhanced resistance to interference from test sample-to-test sample pH variations.

SUMMARY OF THE INVENTION

Briefly, the present invention relates to a test means, device, and method for determining the specific gravity of an aqueous test sample. The test means comprises a weakly basic polyelectrolyte salt, that is, a weakly basic polyelectrolyte polymer which has been at least partially neutralized with a specific strongly acidic organic acid; and an indicator substance capable of producing a detectable response to ion exchange between the polyelectrolyte salt and the test sample. The device of the present invention comprises a carrier matrix incorporated with the test means. The method of the present invention comprises contacting a test sample with the device or test means and observing a detectable response such as a change in color, pH or enzyme activity.

Ideally, the weakly basic polyelectrolyte polymer is at least about 20 percent neutralized. Thus, at least about 20 percent of the basic constituents incorporated in or pendant from the polymer backbone are present in the form of the salt of a strong organic acid.

DEFINITIONS

Certain terms used in the present discussion should at this point be mentioned to assure that the reader is of the same mind as the author as to their respective meanings. Thus the following definitions are provided in order that the reader be fully apprised of the scope of the present invention, and that he be fully enabled to formulate and use it.

1. The term "lower alkyl" includes alkyl groups having one to six carbon atoms. Thus, it includes methyl, ethyl, n-propyl, isopropyl, n-butyl, isobutyl, tert-butyl and all of the pentyl and hexyl isomers. Such groups may be substituted or unsubstituted although, of course, substituents which would adversely affect the use of the invention by being reactive so as to interfere with the intended functions of its components are clearly outside the intended meaning of the term. Such interfering substituents are easily determinable at the laboratory bench through routine experimentation in keeping with the teachings of the present disclosure and the Examples.

2. As used herein, the term "aryl" relates to groups having one or more six-membered ring systems which contain the structure of benzene or other aromatic derivatives. Typical of aryl groups are phenyl ($C_6H_5$—), benzyl ($C_6H_5CH_2$—), and naphthyl. Like the lower alkyl groups, the aryl groups may be substituted or unsubstituted, provided the substituent not interfere with the intended function of the invention, i.e., the measurement of ionic strength or specific gravity.

3. As used herein, the term "alkenyl" is intended as a hydrocarbon group having at least one double bond in its molecular structure, and which contains 1 to about 6 carbon atoms. An alkenyl group may be substituted or unsubstituted, provided the substituent not interfere with the intended function of the invention, i.e., the measurement of ionic strength or specific gravity.

4. By the term "strong organic acid" is meant one which completely or substantially dissociates in aqueous solution.

Stated differently, a strong organic acid is one which has an acidity constant, $K_a$, of more than about $1 \times 10^{-2}$. The strength of an acid HA in a solvent S is usually defined as being proportional to its acidity constant, i.e., the equilibrium constant $K_a$ for the equilibrium $$HA + S \rightleftharpoons A^- + SH^+ \tag{9}$$

$$K_a = \frac{[A^-][SH^+]}{[HA]} \tag{10}$$

In equation (10), the constant concentration of the solvent is included in the value for $K_a$. Since the acidity constant is the ratio of ionized to unionized species, the higher the $K_a$ for a particular organic acid, the greater the extent of the ionization (in a particular solvent system) and the stronger the acid.

In addition to the acidity constant, the acid is also defined as being an organic molecule. Thus the definition also includes lower alkyl, alkenyl and aryl acids.

5. "Polyelectrolyte salt" is intended to mean a weakly basic polyelectrolyte polymer, one or more of the basic moieties of which have been chemically combined, or neutralized, with a strong organic acid. The salt is one in which the neutralized basic constituents of the polymer have been protonated, thereby having acquired a positive charge, and the charge is at least partially neutralized by the organic acid anion.

POLYELECTROLYTES AND THEIR SALTS

Weakly Basic Polyelectrolytes

The presently claimed test means comprises, as one ingredient, a weakly basic polyelectrolyte. Numerous examples of such polymers are known in the art, their common characteristics centering about the presence of basic pendant groups or basic constituents incorporated in the polymer backbone. Most poly-electrolytes are soluble or partially soluble in water, and are readily ionizable, depending on the ionic nature of (a) the aqueous system and (b) the ionizable species on the polymer chain. In the case of weakly basic polyelectrolytes, the basic moiety is usually an amine group (—$NH_2$) or the imino moiety (—NH—). Thus the term does not include poly(vinylammonium hydroxide), but does include such polymers as poly(ethyleneimine), poly(vinylamine), poly(aminostyrene), and various copolymers of ethyleneimine, vinyl amine, aminostyrene, and other monomers. Also included is any weakly basic polymer capable of combining with a strong organic acid to yield a salt capable of producing a pH change ($\Delta$pH) proportional to a corresponding change in the ionic strength of an aqueous solution.

Thus a polyelectrolyte is branded weakly or strongly basic depending on its behavior in solution. Generally, a polyelectrolyte which ionizes to a substantial degree when contacted with water, such as poly(vinylammonium hydroxide) is considered a strong polyelectrolyte. Weakly basic polyelectrolytes on the other hand, contain weakly ionizable groups, such as those mentioned above. The charge density along the molecular chain of these polymers can be varied by varying the degree of substitution, as well as the degree of neutralization.

While the composition and test means of the present invention includes weakly basic polyelectrolytes, at least some of the functional groups of the polymer (e.g. —NH$_2$) are first partially reacted to form a salt, as specified supra. Thus, the polyelectrolyte salt can be prepared by titrating the polymer with a strong organic acid until at least about 20% of the carboxyl groups have been neutralized. Ideally, the polymer is about 20–50% neutralized.

Strong Organic Acids

As stated, supra, the strong organic acids of the present invention are characterized by substantial dissociation in water and/or a relatively high acidity constant. Ideally the acid has a $K_a$ of at least about $1 \times 10^{-2}$. Organic acids having a $K_a$ of less than about $1 \times 10^{-2}$ generally exhibit a substantial buffering effect. Since the invention is dependent upon the detection of a partial shift in pH attributable to the ionic strength of the test sample, substantial buffering by a polyelectrolyte salt of a weak acid would tend to diminish the sought-after effect.

Typical strong organic acids suitable for use in preparing the polyelectrolyte salt of the present invention, and their respective $K_a$ is, are listed in Table I. Of course, this list is exemplary only and acids other than those in the table are included within the scope of the invention.

TABLE I

| Strong Organic Acid | $K_a$ |
| --- | --- |
| benzene sulfinic acid | $3.2 \times 10^{-2}$ |
| benzene sulfonic acid | $2.0 \times 10^{-1}$ |
| 2-bromo-6-nitrobenzoic acid | $4.3 \times 10^{-2}$ |
| 2-chloro-4-nitrobenzoic acid | $1.1 \times 10^{-2}$ |
| 2-chloro-6-nitrobenzoic acid | $4.6 \times 10^{-2}$ |
| 3-chloro-6-nitrobenzoic acid | $1.4 \times 10^{-2}$ |
| 4-chlorophthalic acid | $2.5 \times 10^{-2}$ |
| $\alpha,\alpha$-dibromopropionic acid | $3.3 \times 10^{-2}$ |
| dichloroacetic acid | $5.0 \times 10^{-2}$ |
| 2,6-dihydroxybenzoic acid | $5.0 \times 10^{-2}$ |
| dihydroxyfumaric acid | $7.9 \times 10^{-2}$ |
| dihydroxymaleic acid | $7.1 \times 10^{-2}$ |
| 2,3-dinitrobenzoic acid | $1.4 \times 10^{-2}$ |
| 2,4-dinitrobenzoic acid | $2.4 \times 10^{-2}$ |
| 2,6-dinitrobenzoic acid | $7.2 \times 10^{-2}$ |
| heptafluoro-$\eta$-butyric acid | $6.8 \times 10^{-1}$ |
| 2-hydroxy-3-nitrobenzoic acid | $1.4 \times 10^{-2}$ |
| 8-hydroxyquinoline-5-sulfonic acid | $5.0 \times 10^{-2}$ |
| 2-methyl-6-nitrobenzoic acid | $1.4 \times 10^{-2}$ |
| 4-methyl-2-nitroterephthalic acid | $1.5 \times 10^{-2}$ |
| 1-naphthalene sulfonic acid | $2.7 \times 10^{-1}$ |
| nitroacetic acid | $2.1 \times 10^{-2}$ |
| 3-nitrophthalic acid | $1.3 \times 10^{-2}$ |
| propiolic acid | $1.4 \times 10^{-2}$ |
| sulfamic acid | $1.0 \times 10^{-1}$ |
| $\alpha$-sulfopropionic acid | $1.0 \times 10^{-2}$ |
| p-toluenesulfonic acid | $2.0 \times 10^{-2}$ |
| 2,4,6-tribromobenzoic acid | $3.4 \times 10^{-2}$ |
| trichloroacetic acid | $2.3 \times 10^{-1}$ |
| 2,4,6-trihydroxybenzoic Acid | $2.1 \times 10^{-2}$ |
| 2,4,6-trinitrobenzoic Acid | $2.2 \times 10^{-1}$ |
| 2,4,6-trinitrophenol | $1.6 \times 10^{-1}$ |

Preparation of the Polyelectrolyte Salt

The weakly basic polyelectrolyte salt of the present invention may be prepared by aqueous titration of the polyelectrolyte polymer using a solution of a strong organic acid. The basic constituents of the polymer are preferably at least about 20 percent neutralized. An ideal neutralization range, and that presently found most preferred in the present invention, is from about 20 to about 60% neutralization, 50% having thus far been found to be optimum in providing the largest separation in pH change or other detectable response with respect to specific gravity or ionic strength.

pH INDICATORS MEANS

Another element of the present invention is an indicator means. It can take on such diverse forms as a pH indicator compound, an enzymatic system whose enzyme/substrate function is responsive to subtle pH changes, a pH meter, and a pH-sensitive antigen/antibody system. Thus, known pH-sensitive chromogenic reagent compounds can be employed, and these can provide a change in or appearance of color, observable by the person performing the measurement, which is indicative of the ionic strength or specific gravity of the system being tested. If a chromogen is used, a reference color system can be established beforehand, so that a quick visual comparison of the composition and the reference system provides the sought-after results. Examples of chromogens suitable for use in the present invention are bromothymol blue, alizarin, bromocresol purple, phenol red and neutral red; bromothymol blue having been found to be especially suitable.

Alternatively, the indicator means can take the form of a pH meter, whereby small changes in pH ($\Delta$pH) can be monitored directly, without resorting to visual observation of color change. One particularly suitable approach is to use the pH meter in conjunction with a surface pH electrode. The pH meter response can then be observed over various ionic strength values and a reference system can be established, a particular change in pH corresponding to a particular test sample ionic strength.

Yet another ramification of the indicator means is a pH-sensitive enzyme-based system, whereby subtle changes in pH caused by the polyelectrolyte/ionic strength interaction can trigger the onset of enzymatic activity, or which can change kinetic reaction parameters such as the $K_M$ for a particular enzymatic reaction. Thus an enzymatic system capable of providing a detectable response can be triggered to produce that response in accordance with the specific gravity or ionic strength of a test sample. For example, the enzyme chymotrypsin is known to be sensitive to pH in acting on the substrate p-nitrophenyl acetate to yield the yellow product, p-nitrophenol. The reaction rate dramatically increases from pH 6 to 8 and the appearance of p-nitrophenol is markedly enhanced by pH increases in that range.

Similarly, an antigen-labeled substrate can be employed. The pH dependence of antigen/antibody reactions is well known, and the indicator means of the present invention can include such a labeled substrate and the antibody for the label. Change in pH can be measured by change in substrate available for a corresponding enzymatic reaction.

THE TEST DEVICE

The test device of the present invention comprises a suitable carrier matrix which has been incorporated with a polyelectrolyte salt and an indicator compound or other pH-sensitive means, together with other inert ingredients. In an especially convenient format, a portion of the composition-bearing matrix can be mounted on one end of a plastic strip, the other end serving as a handle. Such a device can then be used to assay the ionic strength or specific gravity of a test sample merely by dipping the matrix into the sample, removing it, and observing the color of the matrix, e.g., by comparing it to a reference color chart.

The Carrier Matrix

The carrier matrix is usually, but not necessarily, a porous substance such as filter paper. Other art-recognized forms of carrier matrix materials are felt, porous ceramic strips, and woven or matted glass fibers (U.S. Pat. No. 3,846,247). Also suggested are the use of wood, cloth, sponge material and argillaceous substances (U.S. Pat. No. 3,552,928). All such carrier matrix materials are feasible for use in the present invention, as are others. It has been found that filter paper is especially suitable.

Incorporation of the Composition With the Matrix

The method by which reagent composition of the present invention is incorporated with a carrier matrix is intended as broad in scope, and depends largely on the nature of the matrix. For example, where the carrier is a polymeric film, the polyelectrolyte salt and pH indicator can be cast as a film by combination in solution either alone or with a suitable binder, followed by application with a doctor blade. Alternatively, the composition can be homogeneously blended with the film polymer, such as by forming a solution of both polymer and composition; or the composition can be blended with melted polymer. The homogeneous blend can then be cast as a film (if the solution approach is adopted), or melted into a film, such as by use of heated platens. Many carrier matrices lend themselves to reagent application using spraying and printing techniques, such as ink jet printing.

In a preferred embodiment, filter paper is wetted with a solution or suspension of the polyelectrolyte salt in water or other convenient excipient and then dried. The polyelectrolyte-bearing filter paper is subsequently incorporated with the desired indicator means. Typically, the paper is wetted with a solution of a pH-sensitive chromogenic indicator (such as bromothymol blue) in methanol or other suitable solvent such as ethanol, N,N-dimethylformamide, or dimethylsulfoxide, and subsequently dried. Alternatively, a one-dip method can be used whereby the polyelectrolyte and indicator means are simultaneously present in the initial solution or suspension.

Preparation of a Dip-and-Read Device

As indicated above, the reagent-bearing carrier matrix can be mounted on a backing material if desired. The test device, in a preferred embodiment, thus comprises a filter paper carrier matrix incorporated with a polyelectrolyte salt and indicator means, the matrix being affixed to one end of an elongated piece of transparent polystyrene film, the other end serving as a handle. The matrix is secured to the film by any suitable means, for example by using double-faced adhesive tape (Double Stick ® available from 3M Company). In use, such a device is held by the free end of the polystyrene film backing material and the matrix end is immersed into the test sample (e.g., urine) and quickly removed. Any color formation or other detectable response is observed after a predetermined time and compared with a color reference standard corresponding to responses to known solution ionic strengths or specific gravities.

REFERENCE STANDARD

The particular reference standard employed depends on whether the test means is used by itself or incorporated with a carrier matrix, and depends as well on the particular indicator means employed. Thus, if the polyelectrolyte salt is added directly to the test sample and the indicator means is a pH meter, a reference standard can be devised by adding a standard weight of polyelectrolyte salt to a standard volume of a solution of known ionic strength. The pH before and after polyelectrolyte salt addition is recorded using the pH meter. This procedure is followed for a series of solutions having differing known ionic strengths. To determine the ionic strength of an unknown test sample, the same procedure is followed and the pH change compared with those of the known solutions.

Where a test device comprising a carrier matrix containing polyelectrolyte salt and a colorometric pH indicator is employed, a reference standard can comprise a series of color blocks depicting the color developed by the carrier matrix after a predetermined time in response to solutions of known ionic strengths. When testing an unknown sample, the carrier matrix of a test device is immersed in the sample, removed, and observed for the appearance of or change in color after the predetermined time. The carrier matrix is at that time compared with the reference standard color blocks to ascertain the ionic strength or specific gravity of the sample.

EXAMPLES

The following examples are provided to further assist the reader in making and using the present invention. Thus, preferred embodiments are described and analyzed. The Examples are meant to be illustrative only, and are in no way intended as limiting the scope of the invention described and claimed hereto.

Preparation of Polyelectrolyte Salts

A series of experiments was conducted to prepare salts of weakly basic polyelectrolytes with various strong organic acids. The polyelectrolyte employed was poly(ethyleneimine) obtained from Polysciences, Inc. as a 30% aqueous solution, and the strong organic acids employed were trichloroacetic acid and benzenesulfonic acid.

To a 25 milliliter (ml) aliquot of a solution of poly(ethyleneimine) having a concentration of 1.24% (grams (g) of polymer per 100 ml of solution) was added, successively, 0.5 ml portions of 26.1% benzene sulfonic acid with stirring. This 0.5 ml portion of strong acid is sufficient to neutralize about 10% of the imine groups in the polyelectrolyte. After each addition of 0.5 ml of acid solution, the reaction mixture was allowed to reach equilibrium and the pH was recorded.

A similar titration was carried out using identical solutions except that the polymer solution was made 1.1M in NaCl. The difference in pH between the polyelectrolyte titration in distilled water and that in the NaCl solution is indicative of the ability of the polyelectrolyte salt to measure ionic strength. The data is presented in Table II.

TABLE II

| Degree of | pH of Polymer Solution | | |
|---|---|---|---|
| Neutralization (%) | in Water | in 1.1 M NaCl | Δ pH |
| 0 | 10.17 | 10.84 | 0.67 |

TABLE II-continued

| Degree of Neutralization (%) | pH of Polymer Solution in Water | pH of Polymer Solution in 1.1 M NaCl | Δ pH |
|---|---|---|---|
| 10 | 9.07 | 9.99 | 0.92 |
| 20 | 8.36 | 9.39 | 1.03 |
| 30 | 7.50 | 8.66 | 1.16 |
| 40 | 6.06 | 7.33 | 1.27 |
| 50 | 4.33 | 5.73 | 1.40 |
| 60 | 2.39 | 2.95 | 0.56 |
| 70 | 1.62 | 1.62 | 0.00 |
| 80 | 1.32 | 1.27 | −0.05 |
| 90 | 1.15 | 1.08 | −0.07 |
| 100 | 1.03 | 0.94 | −0.09 |

The data shows that a solution having a significant ionic strength causes an equally significant shift in pH in the presence of the polyelectrolyte salt of poly(ethyleneimine) and benzenesulfonic acid. Moreover, this change in pH (ΔpH) is maximized when the polymer is 20 to 60% neutralized, and 50% neutralization provides the largest ΔpH (1.40) with 1.1M NaCl.

The foregoing experiment was repeated except that trichloroacetic acid was substituted. Thus, 25 ml of 1.24% poly(ethyleneimine) in distilled water was titrated successively with 0.5 ml of a 25% solution of trichloroacetic acid. Each 0.5 ml aliquot of acid corresponds to 10% titration of the imino moieties of the polyelectrolyte. After each addition of 0.5 ml of acid, the resultant solution was permitted to equilibrate, and the pH measured.

A similar titration was carried out using a second 25 ml aliquot of the polyelectrolyte solution except that prior to titration sufficient NaCl was added to make the solution 1.1M in NaCl. The resultant pH was measured after each 0.5 ml of acid had been added. The difference in pH between the polyelectrolyte in water and in 1.1M NaCl is indicative of the ability of poly(ethyleneimine) trichloroacetate to measure ionic strength. The data is recorded in Table III.

The data shows that a significant shift in pH (ΔpH) from that of aqueous polyelectrolyte salt solution occurs when the ionic strength of the solution changes. Moreover, ΔpH is maximized when the polymer is 20 to 60% neutralized, and 50% neutralization provides the largest ΔpH (1.40) with 1.1M NaCl.

TABLE III

| Degree of Neutralization (%) | pH of Polymer Solution in Water | pH of Polymer Solution in 1.1 M NaCl | Δ pH |
|---|---|---|---|
| 0 | 10.19 | 10.81 | 0.62 |
| 10 | 9.10 | 10.01 | 0.91 |
| 20 | 8.37 | 9.44 | 1.07 |
| 30 | 7.59 | 8.79 | 1.20 |
| 40 | 6.34 | 7.64 | 1.30 |
| 50 | 4.82 | 6.22 | 1.40 |
| 60 | 2.81 | 4.18 | 1.37 |
| 70 | 1.81 | 2.01 | 0.20 |
| 80 | 1.44 | 1.45 | 0.01 |
| 90 | 1.23 | 1.20 | −0.03 |
| 100 | 1.11 | 1.05 | −0.06 |

Preparation of Polyelectrolyte Salts With HCl

In order to provide a basis for comparison, poly(ethyleneimine) was titrated with HCl instead of the strong organic acid of the present invention. Thus 25 ml of 1.24% poly(ethyleneimine) was titrated with 0.5 ml aliquots of 0.0274% HCl. The solution was allowed to equilibrate after each addition and the pH measured.

A similar titration was carried out using 25 ml of the polymer solution which had been made 1.1M in NaCl. The data is plotted in Table IV, which shows that the ΔpH for 1.1M NaCl is much less using poly(ethyleneimine) hydrochloride than for the present invention salts in 10.1, supra.

TABLE IV

| Degree of Neutralization (%) | pH of Polymer Solution in Water | pH of Polymer Solution in 1.1 M NaCl | Δ pH |
|---|---|---|---|
| 0 | 10.18 | 10.75 | 0.57 |
| 10 | 9.09 | 9.95 | 0.86 |
| 20 | 8.40 | 9.38 | 0.98 |
| 30 | 7.63 | 8.67 | 1.04 |
| 40 | 6.35 | 7.37 | 1.02 |
| 50 | 4.91 | 5.85 | 0.94 |
| 60 | 3.01 | 3.77 | 0.76 |
| 70 | 1.88 | 1.80 | −0.08 |
| 80 | 1.47 | 1.34 | −0.13 |
| 90 | 1.25 | 1.12 | −0.13 |
| 100 | 1.11 | 0.97 | −0.14 |

Comparison of Results

The results of the Examples 9.1 and 9.2 are compared in Table V. The data shows that substantial ΔpH values occurred in response to ionic strength with poly(ethyleneimine) salts of benzenesulfonic acid and trichloroacetic acid. Similar polymer salts of HCl gave dramatically reduced results. At 50% neutralization both salts of the instant invention gave ΔpH values 49% greater than the HCl salt. Throughout the effective range of neutralization, i.e., 20 to 60%, the HCl salt consistently yielded appreciably lower ΔpH values.

TABLE V

| Degree of Neutralization | Δ pH HCl | Δ pH Benzenesulfonic acid | Δ pH trichloroacetic acid |
|---|---|---|---|
| 0 | 0.57 | 0.67 | 0.62 |
| 10 | 0.86 | 0.92 | 0.91 |
| 20 | 0.98 | 1.03 | 1.07 |
| 30 | 1.04 | 1.16 | 1.20 |
| 40 | 1.02 | 1.27 | 1.30 |
| 50 | 0.94 | 1.40 | 1.40 |
| 60 | 0.76 | 1.56 | 1.37 |
| 70 | −0.08 | 0.00 | 0.20 |
| 80 | −0.13 | −0.05 | 0.01 |
| 90 | −0.13 | −0.07 | −0.03 |
| 100 | −0.14 | −0.09 | −0.06 |

What is claimed is:

1. In a test means for determining the ionic strength or specific gravity of an aqueous test sample, wherein the test means comprises a weakly basic polyelectrolyte polymer, and an indicator means capable of producing a detectable response to ion exchange between said polyelectrolyte and said sample;

the improvement wherein 20 to 60% of the basic moieties of said polyelectrolyte is present as a salt of a strong organic acid.

2. The improved test means of claim 1 in which about 50% of the basic moieties of said polymer are in the form of a salt of said acid.

3. The improved test means of claim 1 in which the polyelectrolyte is poly(ethyleneimine), poly(vinylamine), poly(aminostyrene) or copolymers thereof.

4. The improved test means of claim 1 in which the polyelectrolyte is poly(ethyleneimine).

5. The improved test means of claim 1 in which the acid has an acidity constant, $K_a$, of at least about $1 \times 10^{-2}$.

6. The improved test means of claim 1 in which the acid is benzenesulfonic acid or trichloroacetic acid.

7. The improved test means of any one of claims 1-6 in which the indicator means is a pH indicator substance.

8. The improved test means of claim 7 in which the pH means is bromothymol blue.

9. A test device for determining the ionic strength or specific gravity of an aqueous test sample, the device comprising a carrier matrix incorporated with the test means of claim 7.

10. A method for determining the ionic strength or specific gravity of an aqueous test sample, the method comprising contacting the sample with the test means any one of claims 1-6 and observing a detectable response.

11. A method for determining the ionic strength or specific gravity of an aqueous test sample, the method comprising contacting the sample with the test device of claim 9 and observing a detectable response.

12. A method for preparing a test device for determining the ionic strength or specific gravity of an aqueous test sample, the method comprising the steps of reacting a weakly basic polyelectrolyte polymer with sufficient strong organic acid to form a salt of about 20 to 60% of the basic moieties of the polyelectrolyte, thereby forming a polyelectrolyte salt, and incorporating a carrier matrix with the polyelectrolyte salt and a pH indicator substance.

* * * * *